United States Patent [19]

Kenna

[11] Patent Number: 4,828,562
[45] Date of Patent: May 9, 1989

[54] ANTERIOR CRUCIATE LIGAMENT PROSTHESIS

[75] Inventor: Robert V. Kenna, Hobe Sound, Fla.

[73] Assignee: Pfizer Hospital Products Group, Inc., New York, N.Y.

[21] Appl. No.: 152,129

[22] Filed: Feb. 4, 1988

[51] Int. Cl.$^4$ ............................................. A61F 2/08
[52] U.S. Cl. ................................. 623/13; 128/92 YF; 623/20
[58] Field of Search ........................... 623/13, 16, 20; 128/92 YF

[56] References Cited

U.S. PATENT DOCUMENTS

| | | | |
|---|---|---|---|
| 3,953,896 | 5/1976 | Treace | 623/13 |
| 4,301,551 | 11/1981 | Dore et al. | 623/13 |
| 4,400,833 | 8/1983 | Kurlund | 623/13 |
| 4,597,766 | 7/1986 | Hilal et al. | 623/13 |
| 4,605,414 | 8/1986 | Czajka | 623/13 |

Primary Examiner—Ronald L. Frinks
Attorney, Agent, or Firm—Peter C. Richardson; Lawrence C. Akers; Elizabeth O. Slade

[57] ABSTRACT

An adjustable housing suitable to be used with another housing and with a synthetic ligament so as to provide (for example) an anterior cruciate ligament prosthesis system for a knee joint is provided. The adjustable housing features an interior having a step shoulder located therein. A set screw in the housing fixes the synthetic ligament at a desired level of tension. The system has many significant advantages including (but not limited to) being able to withstand very high loads and being able to be retensioned repeatedly and easily without replacing the artificial ligament.

16 Claims, 3 Drawing Sheets

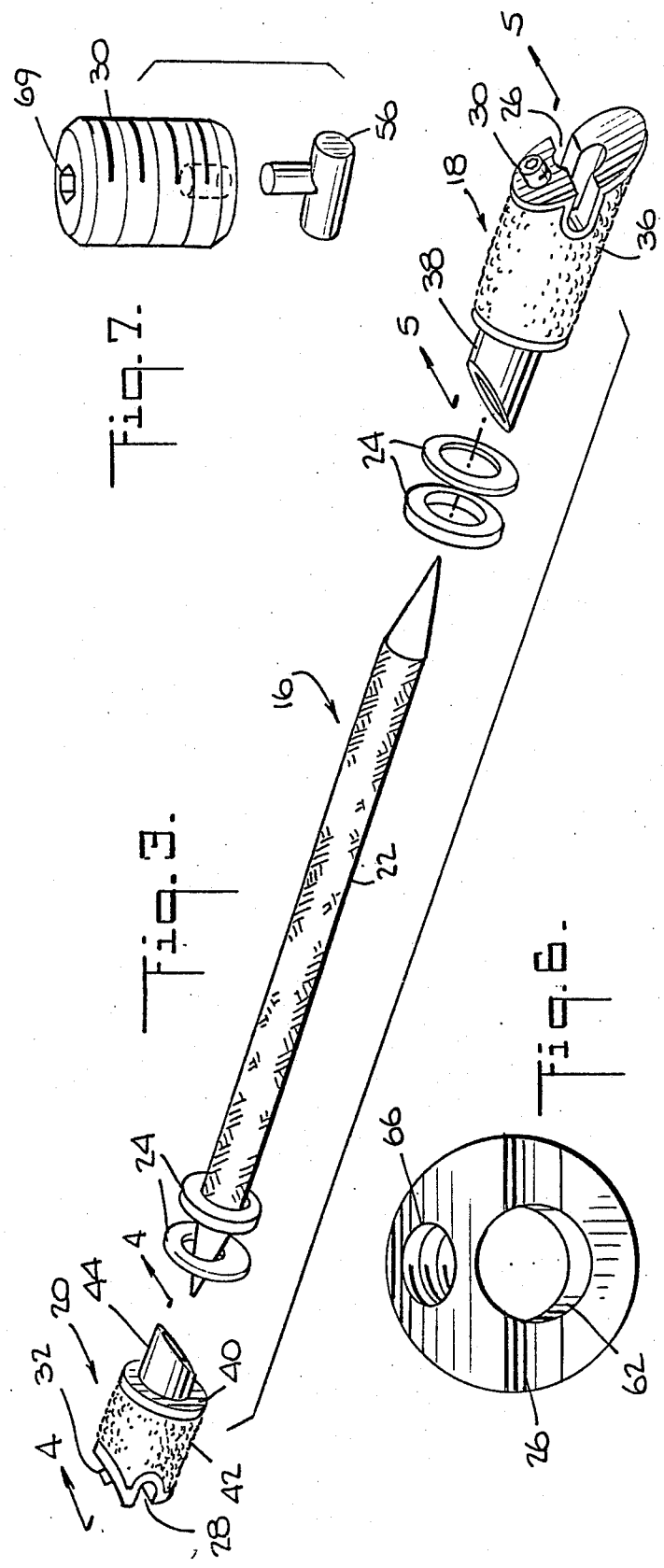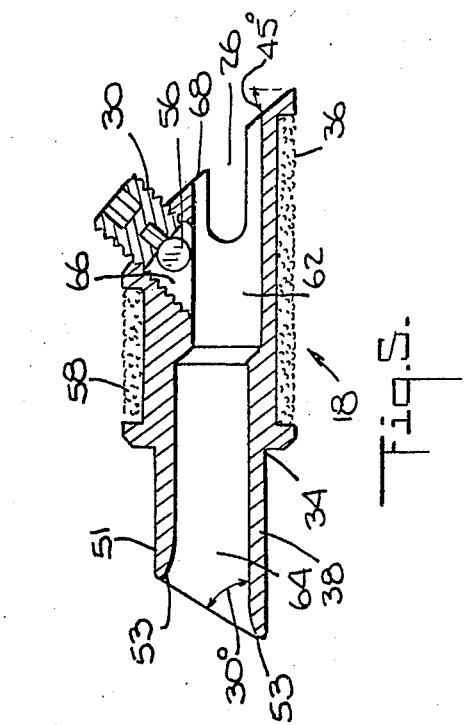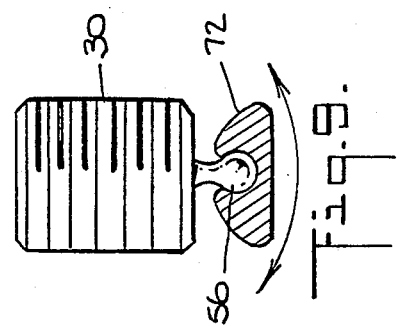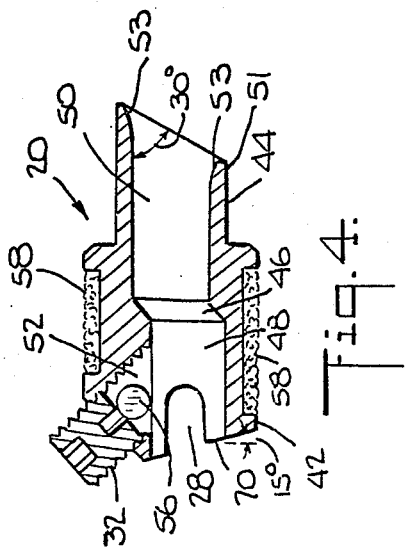

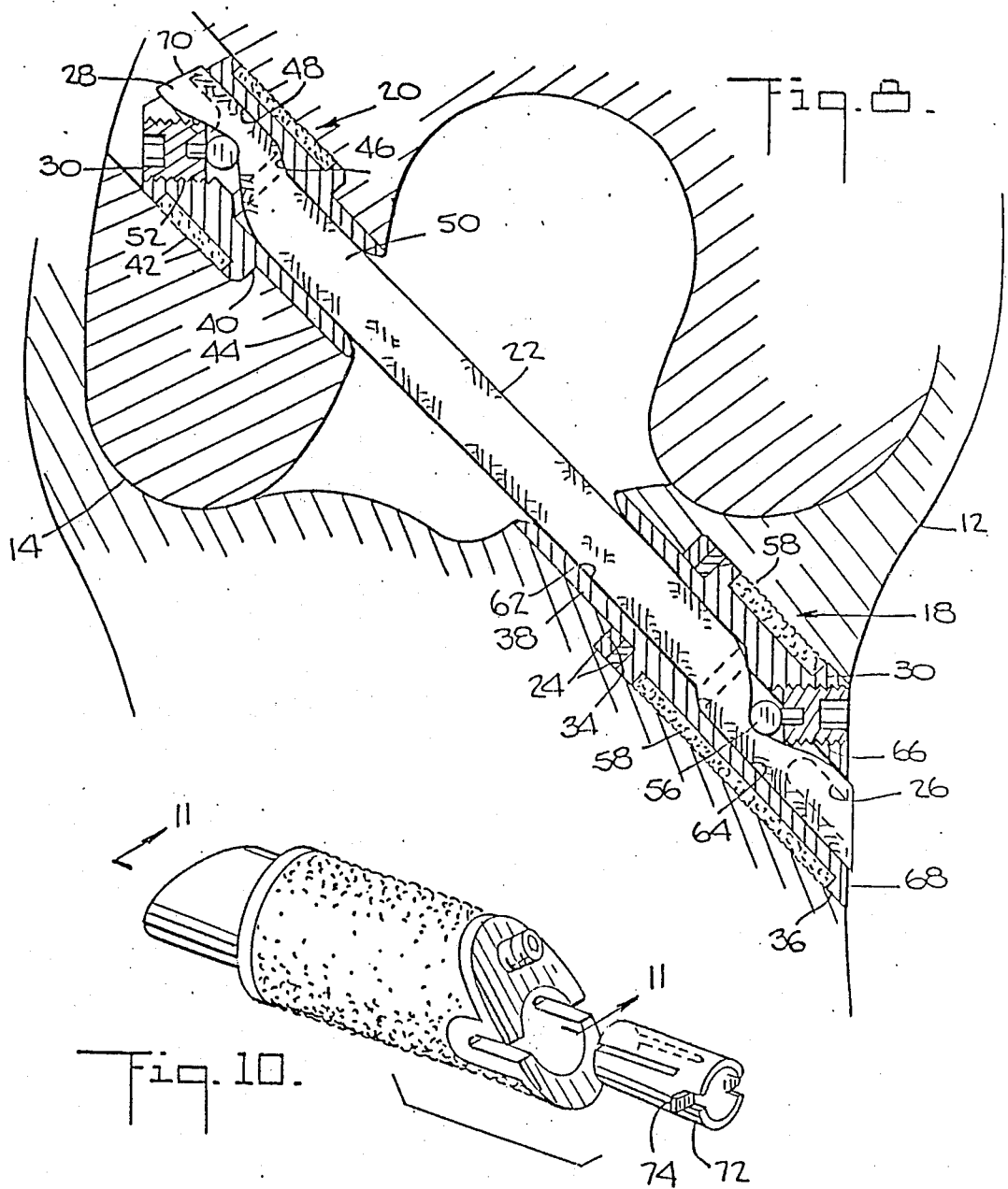
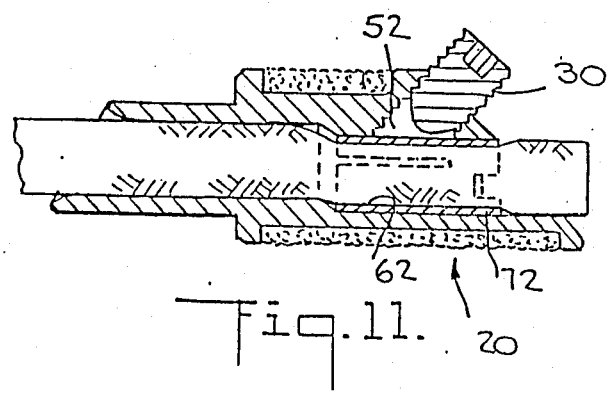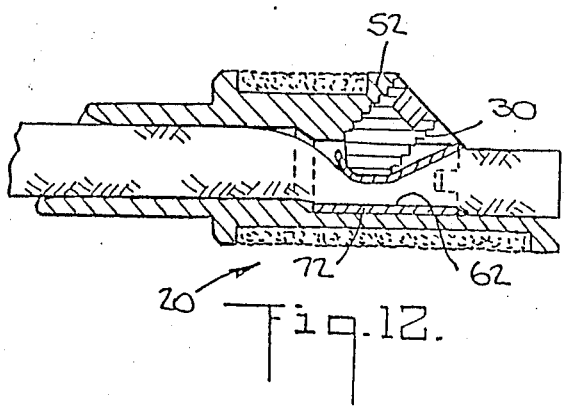

ANTERIOR CRUCIATE LIGAMENT PROSTHESIS

BACKGROUND OF THE INVENTION

In the field of orthopedics, rupture of anterior cruciate ligaments has been a problem which has been addressed by various solutions. See, for example, U.S. Pat. No. 4,605,414 to Czajka, "Reconstruction of a Cruciate Ligament"; U.S. Pat. No. 4,400,833, to Kurland, "Means and Method of Implanting Bioprosthetics"; and U.S. Pat. No. 3,797,047 to Pillet, "Artificial Tendon."

However, despite this and other work, a need has continued to exist for a system which can withstand higher loads than have previously been possible, which permits an unlimited number of retensionings to be made, and in which it is not difficult to replace a synthetic tendon.

To date, such a system has not previously been known

OBJECTS OF THE INVENTION

It is an object of this invention to provide a system for replacement of a natural anterior cruciate ligament having excellent strength properties, excellent short and long term stability, and ability to undergo a very large number of retensionings without replacement of the artificial ligament; however, if replacement of that ligament is required, it can easily be accomplished.

A further object of this invention is a fixator or housing suitable for use in an anterior cruciate ligament prosthesis system which has great strength, retensioning capabilities, short and long stability, and in which parts can be rapidly and simply replaced.

A further object of this invention is an improved system for an anterior cruciate ligament prosthesis in which either one or multiple cords can, if desired, be used.

Yet another object of this invention is a method for positioning an anterior cruciate ligament prosthesis within a knee joint.

A further object of this invention is a method of replacing an anterior cruciate ligament within a knee joint without removing the housings.

SUMMARY OF THE INVENTION

These and other objects are satisfied by the anterior cruciate ligament prosthesis of the invention which comprises an adjustable housing to be relatively permanently implanted into a bone bore in either the tibia portion (or the femoral portion) of a knee joint, the adjustable housing having the following features, including a step shoulder located therein which connects a first bore and a second bore which are not coaxial but which are both located substantially longitudinally within the adjustable housing, the adjustable housing having also a third bore which intersects the step shoulder at an angle of about 90° and which is adapted to house a set screw.

Preferably, the adjustable housing will be relatively permanently implanted into the tibia portion of a knee joint and will be used with a second housing which is relatively permanently implanted into the femur portion of the knee joint. The second housing can be but need not be an adjustable housing as described above.

Further, according to the invention, the step shoulder preferably intersects both the first bore and the second bore at an angle of about 45°, although any angle greater than 0° and less than about 90° is within the scope of this invention.

Further, according to the invention, the adjustable housing is in the form of a step drill made up of a larger diameter substantially cylindrical portion which is joined to a smaller diameter substantially cylindrical portion.

Additionally, according to the invention, a method of positioning and fixing an anterior cruciate ligament prosthesis within a knee joint comprises (a) fixing a ligament housing having a longitudinal bore within a bone bore in either the femoral or tibial side of a knee joint, in such a manner that the ligament housing is substantially permanently fixed within the bone bore and in such a manner that the housing has a first end of an artificial ligament extending therefrom and has a second end of the artificial ligament fixed by the ligament housing; (b) threading the first end of the artificial ligament through an adjustable housing according to the invention; (c) inserting the adjustable housing into the bone bore in the other side of the knee joint so that one housing is in the tibial portion and one housing is in the femoral portion; (d) adjusting the tension of the artificial ligament as desired; (e) inserting the set screw into the third bore of the adjustable housing according to the invention so that the set screw abuts against and securely fixes the artificial ligament.

Also, according to the invention, in a preferred embodiment, the adjustable housing is placed into a bore in the tibial side of the knee joint.

DESCRIPTION OF THE PREFERRED EMBODIMENTS

BRIEF DESCRIPTION OF THE DRAWINGS

FIG. 3 is a plan view of a preferred embodiment of a prosthesis system according to the invention, including various parts of that preferred embodiment useful for replacing the normal anterior cruciate ligament.

FIG. 4 is a cross-sectional view, taken along the line 4—4 in FIG. 3, of a preferred embodiment of a housing according to the invention for placement preferably into a femoral portion of a knee joint, showing a step shoulder, set screw, slot, and porous coating.

FIG. 5 is a view in cross section taken along the line 5—5 of FIG. 3, showing a preferred embodiment of the housing of the invention suitable for placement preferably into a tibial portion of a knee joint.

FIG. 6 is an elevational view of either housing shown in FIG. 3.

FIG. 7 is a plan view showing a set screw, together with a "tee" bar which is to be used in a preferred embodiment according to the invention.

FIG. 8 is a cross-sectional view of a preferred embodiment of an anterior cruciate ligament prosthesis system according to the invention when it is implanted into a knee joint, showing the positioning and shape of a preferred embodiment according to the invention of an adjustable housing (on the lower right hand portion of FIG. 8) for use preferably in a tibia part of a knee joint, the exterior surface of that housing being flush with the surface of the tibia and showing an adjustable housing (in the upper, left-hand corner of FIG. 8) for use preferably in the femur part of a knee joint.

FIG. 9 is a plan view showing a set screw with a ball fixed within the set screw which abuts against a portion of a metal sleeve. This is an alternative embodiment to the set screw with "tee" bar shown in FIG. 7.

FIG. 10 is an elevational view of an embodiment of an adjustable housing according to the invention for use in an anterior cruciate ligament prosthesis system, showing a metal sleeve with a tab portion to be inserted into the housing so that the set screw will contact the metal sleeve when the set screw is inserted into the housing.

FIG. 11 is a cross-sectional view, taken along the line 11—11 in FIG. 10.

FIG. 12 is a cross sectional view, taken along the line 11—11 in FIG. 10, after the set screw has been inserted into the housing and contacts the metal sleeve.

DETAILED DESCRIPTION OF THE DRAWINGS

Figure 1:
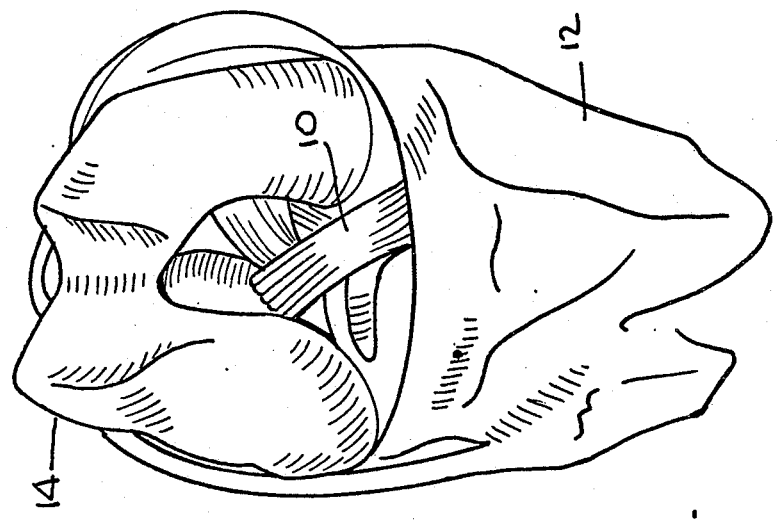
FIG. 1 is a pictorial representation of a normally occurring, healthy anterior cruciate ligament.

In FIG. 1, a pictorial representation of a normal anterior cruciate ligament 10 is shown, together with the tibial portion 12 of a knee joint and a femoral portion 14 of that knee joint.

Figure 2:
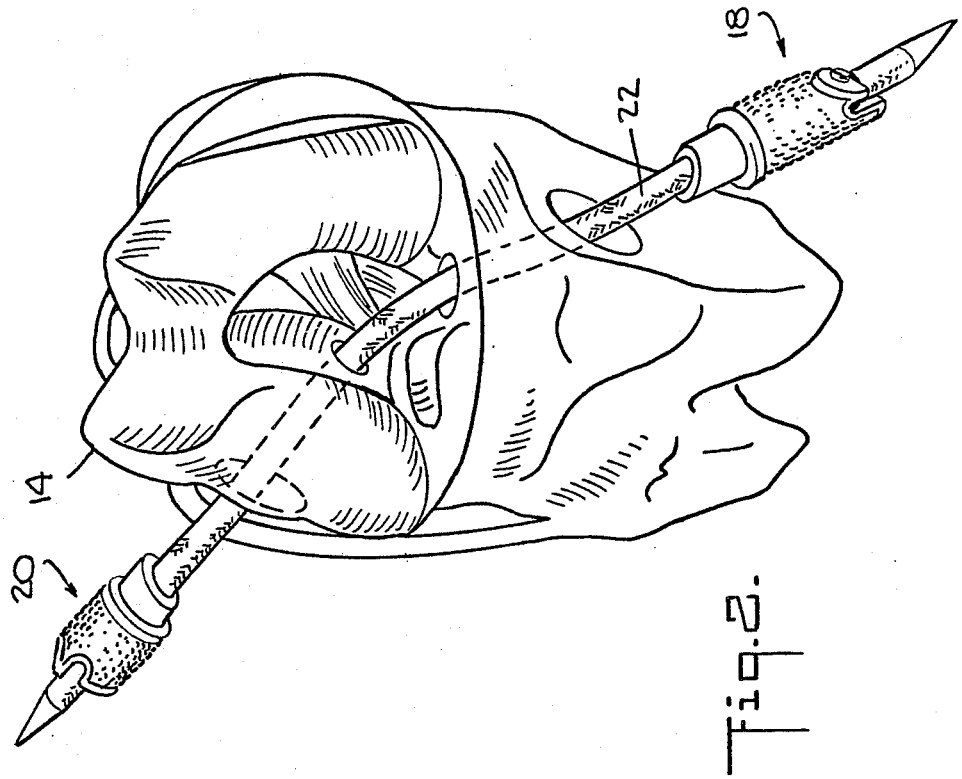
FIG. 2 is a pictorial representation of a system of a preferred embodiment of a prosthetic replacement for the normal anterior cruciate ligament, according to the invention.

In FIG. 2, a preferred embodiment of an anterior cruciate ligament prosthesis 16 according to the invention is shown generally, located within a knee joint.

In FIG. 3, an exploded view of an anterior cruciate ligament prosthesis system 16 according to the invention is shown, with component parts tibial housing 18, femoral housing 20, filament 22 (also referred to as an artificial ligament or artificial tendon), and spacers 24.

Also shown in FIG. 3 are slots 26 and 28 and set screws 30 and 32 located in tibial portion 18 and femoral portion 20, respectively.

Also shown in FIG. 3 is step drill 34 made up of larger diameter cylindrical portion 36 and smaller diameter cylindrical portion 38. Likewise, femoral portion 20 has a step drill 40 made up of larger diameter cylindrical portion 42 and smaller diameter cylindrical portion 44.

FIG. 4 is a cross-sectional view, taken along the line 4—4 in FIG. 3. A step shoulder 46 connects a first bore 48 located in larger diameter cylindrical portion 42 with a second bore 50 located in smaller diameter cylindrical portion 44. It is noted that second bore 50 is a substantially longitudinal bore and is located in a substantially centered position within smaller diameter cylindrical portion 44, whereas first bore 48 is located substantially longitudinally within larger diameter cylindrical portion 42 but is not centered therein.

Also shown in FIG. 4 is a third bore 52 located within femoral housing 20. Set screw 54 is adapted to be positioned within third bore 52 and is intersected on its interior end by "tee bar" 56 (also shown in FIG. 7).

Also shown is a porous metal coating 58 located on the exterior of larger diameter cylindrical portion 42 of femoral housing 20.

In FIG. 5, a cross-sectional view taken along the line 5—5 in FIG. 3 shows tibial housing 18 with larger diameter cylindrical portion 36 having a porous metal coating 58 and smaller diameter cylindrical portion 38. Also shown is step shoulder 60 connecting first bore 62 and second bore 64. Set screw 30 is located within third bore 66. Surface 68 is angled so that when tibial housing 18 is suitably inserted into a bore in the tibia, surface 68 will be flush with the exterior surface of the tibia. Surface 68 is shown in FIG. 5 making an angle of 45° with the vertical.

In FIG. 7, a set screw 30 (with a hexagonal indentation 69) is shown, with a "tee" bar shown for use therewith.

In FIG. 8, is shown a preferred embodiment of the apparatus of the invention, as was shown and described in FIGS. 3-7, implanted within a tibia portion 12 of a knee joint and a femur portion 14 of that knee joint. It is noted that surface 68 is flush with the surface of tibia 12, and surface 70 (also shown in FIG. 4) is preferably slightly below the surface of femur 14. Surface 70 is shown in FIG. 4 at an angle of 15° with the vertical. Filament 22 is shown in a taut position.

In FIG. 9, is shown a set screw 30 having an integrally attached metal ball 56 which abuts against metal sleeve 72.

The nose 51 of the housings sections 38, 44 has a internal radius 53 designed to protect ligament material from fraying relative to range of motion.

In FIG. 10, metal sleeve 72 is shown in greater detail, with a tab portion 74 (which fits into key 76 in tibial housing 18).

In FIG. 11, which is a cross-sectional view taken along the line 11—11 in FIG. 10, set screw 30 is shown positioned within third bore 66 in a tibial housing 18, together with metal sleeve 72 located within first bore 62 in tibial portion 18. Set screw 30 is shown not yet contacting metal sleeve 72, and no "tee" bar is shown in this figure.

In FIG. 12, also taken along the line 11—11 in FIG. 10, set screw 30 is shown in its fully implanted position, contacting metal sleeve 72.

In the practice of the invention, it is required that at least one of the two housings used in the anterior cruciate ligament prosthesis system of the invention be adjustable, and it is preferred that the housing portion which is implanted into the tibia be the adjustable portion. An adjustable housing according to the invention can be used, if desired, with another adjustable housing according to the invention; or an adjustable housing of the invention can be used with any other suitable means for fixing one end of an artificial ligament. An adjustable housing according to the invention can be used to house a single filament (or artificial ligament or tendon), or alternatively, if desired, can be used with two or more ligaments, each filament preferably having its own first, second, and third bores located within the adjustable housing.

A step shoulder located within the adjustable housing connects two longitudinal bores located within the housing, and preferably it connects those two bores such that the step shoulder intersects each bore at an angle greater than 0° and less than about 90°, preferably at about 45°, and most preferably at 45°. A third bore located within the housing is adapted to house a set screw so that the ligament can be passed through the first bore and second bore of the adjustable housing and contacted by the set screw (and thereby held in place).

Preferably, the adjustable housing is in the form of a step drill, having a larger diameter cylindrical portion and a smaller diameter cylindrical portion. This feature provides initial stability to the prosthesis when it is implanted into a bone bore.

When a porous metal coating 58 is located on the housing, preferably on the outer surface of the larger diameter cylindrical portion, bone can grow into the housing and provide long term stability.

However, because of the cylindrical shape, if necessary the housing can be cut from the bone interface with a core drill and relatively easily removed.

Preferably, a slot is located on the outer surface of the housing and is useful for aligning the prosthesis within the bone bore.

Preferably a metal sleeve (made of thin metal and crimped) is placed onto the ligament, such that the set screw will rotate on a piece of static metal (provided by the metal sleeve) when the ligament is fixed by the set screw. The sleeve is preferably split so that the set screw collapses the sleeve. Only the tab drives into the ligament, not the set screw. This preferred sleeve prevents fraying of the ligament by the set screw.

The set screw(s) can be any suitable set screw(s), for example hexagonally indented set screw(s). Importantly, the set screw should meet the step shoulder within the housing at an angle which is about 90°. This angle prevents fraying of the artificial ligament.

If an adjustable housing is to be used for multiple cords, a set screw will be placed across each shoulder located within the housing such that each set screw contacts a ligament located within a shoulder at an angle of about 90°.

Spacers (which are conveniently available in 1 mm or 2 mm sizes) can be used with the prosthesis of the invention if necessary, for example, if the surgeon has overdrilled the bone bore in the tibia or in the femur.

Within the housing, the set screw (or screws, if multiple filaments are being used) clamps down on the filament, locking it in place. The "tee" bar which is free to swivel within the set screw provides a surface which does not fray the cord or ligament. The step shoulder located within the housing provides additional support against slippage of the filament within the housing. It is preferred that the length of the step shoulder be such that both the first bore and the second bore within the housing intersect that step shoulder at an angle of about 45°.

Preferably a solid core filament is used in the prosthesis of the invention. However, other types of filaments can also be used, if desired. For example, a hollow core filament could be used, especially if a solid core portion were inserted into each end of the hollow core, to be contacted by preferably a metal sleeve which is contacted by a set screw within an adjustable housing.

The anterior cruciate ligament prosthesis system according to the invention exhibits the following advantages and characteristics. The fixators or housings generally will not be changed. This is quite different from what has been known in the prior art. In the prosthesis of this invention, the ligament tension can be adjusted or the ligament can be exchanged very rapidly and simply. Multiple tension adjustments can, also, be made before implanting surgery has been completed. A very stable device capable of withstanding very large loads is provided by the device of the invention. It is believed that the prosthesis of the invention is capable of withstanding significantly higher loads than other anterior cruciate ligament prostheses which have previously been known.

The adjustable housing of the invention (as shown in FIGS. 3, 4 and 5), is preferably made by the following procedure. A housing having a larger and a smaller diameter cylindrical portion can be made by any suitable procedure. Also, any suitable procedure for producing a first, second and third bore (as described above) within the housing can be used.

A channel is cut for the porous metal coating 58. Porous metal coating 58 is preferably a 2-layer metal coating, deposited preferably by the procedure as described in U.S. Pat. No. 4,550,448 to Kenna. That patent is hereby incorporated herein by reference.

Filament or synthetic ligament 22, which preferably is a solid core filament, can be made by any suitable procedure.

The anterior cruciate ligament prosthesis according to the invention can be positioned in the knee joint preferably in the following manner. First a relatively small diameter bore is drilled through the tibial and femoral portions of the knee joint bones in any suitable manner. The bore must be large enough to house the synthetic ligament.

Next, a larger diameter bore is made to a depth in the bone equal to the length of the housing to be implanted into the tibial or femoral portion of the knee joint. The diameters of the bores should be chosen so as to contain the housings to be implanted. Then a housing is positioned and relatively permanently fixed on the femoral side of the bone bore with a first end of a filament 22 extending from the housing and extending through the bone bore. The second end of the filament is fixed by (or within) the ligament housing. The first end of the filament 22, which exits from the bone bore is then passed into the second bore 64 (located within the smaller diameter cylindrical portion) of the tibial housing 18, past the step shoulder 60, and then into and through the first bore 62 in the larger diameter cylindrical portion of tibial housing 18, such that the free end of filament 22 extends from the housing 18. The filament 22 is then pretensioned with, for example, a spring-loaded device; and the tension is either increased or decreased. The ligament is then fixed in place by turning down set screw 30 so that "tee" bar 56 contacts the ligament 22 or preferably the metal sleeve 72.

If two adjustable housings are used in the system, and if it is desired to replace the ligament 22, the surgeon can merely back off set screws 30 and 32 and thread through the two housings a new ligament 22. The set screws 30 and 32 can then be repositioned, once the desired tension has been achieved.

It is believed that the adjustable housing of the invention can be used for other uses, wherever there is a need for an adjustable housing having the advantages as described above.

I claim:

1. An anterior cruciate ligament prosthesis comprising:
    a first housing to be implanted into a bone bore drilled in the bone of a first portion of a knee joint selected from the group consisting of a tibia portion of a knee joint and a femur portion of a knee joint,
    said first housing containing a step shoulder which connects a first bore and a second bore (wherein said first bore and said second bore are both located substantially longitudinally within but both are not located coaxially within said first housing),
    said first housing comprising also a third bore having a centerline which intersects said step shoulder at an angle of about 90°, said third bore being adapted to house a set screw, and
    said first housing being adapted to be used with a second housing to be implanted into the other of either a tibia or a femur.

2. A device according to claim 1, wherein said step shoulder connects with said first bore at an angle of about 45° and wherein said step shoulder connects with said second bore at an angle of about 45°.

3. A device according to claim 2, wherein said first housing comprises a step drill made up of a larger diameter substantially cylindrical portion joined to a smaller diameter substantially cylindrical portion and wherein said larger diameter substantially cylindrical portion houses said first bore and said smaller diameter substantially cylindrical portion houses at least a portion of said second bore.

4. A device according to claim 3, wherein said second housing is substantially similar to said first housing.

5. A device according to claim 3, wherein said first housing has a slot located at the outer extremity of said larger diameter cylindrical portion of said housing and wherein said slot is suitable for aiding in positioning said first housing.

6. A device according to claim 3, wherein said first housing has a porous metal coating located on the outer cylindrical surface of said larger diameter substantially cylindrical portion.

7. A device according to claim 6, and including also a metal sleeve which is substantially cylindrical in shape and which has a diameter slightly smaller than the diameter of said first bore wherein said metal sleeve is adapted to contain a filament and then be inserted into said first portion so as to provide a metal surface to be contacted by a set screw.

8. A device according to claim 7, wherein said metal sleeve comprises at least one tab portion located therein which is to be used for aligning said metal sleeve.

9. A device according to claim 8, and including also a spacer in the shape of an annulus having an internal diameter substantially equal to the outer diameter of said smaller diameter cylindrical portion of said first housing.

10. A device according to claim 9, and including also a set screw which is adapted to be secured within said third bore.

11. A device according to claim 10, and including also a solid core filament, wherein said filament is positioned within said first housing and fixed by means of said set screw within said first housing and wherein said filament is also to be similarly positioned within said second housing.

12. A method of positioning an anterior cruciate ligament prosthesis within a knee joint, said method comprising: (a) fixing a ligament housing having a longitudinal bore within a bone bore in a first portion of a knee joint selected from the group consisting of a tibia portion and a femur portion of said knee joint, in such a manner that said ligament housing is substantially permanently fixed within said bone bore, and in such a manner that said housing has a first end of an artificial ligament extending therefrom and extending through said bone bore and has a second end of said artificial ligament fixed by said ligament housing; (b) threading said first end of said artificial ligament through an adjustable first housing according to claim 1; (c) inserting said adjustable first housing into the bone bore in a second portion of said knee joint so that said adjustable first housing is substantially permanently fixed within said bone bore; (d) adjusting the tension of said artificial ligament as desired; and (e) inserting said set screw into said third bore of said adjustable first housing according to claim 1, so that said set screw abuts against said artificial ligament.

13. A method according to claim 12 wherein said first portion of said knee joint is a femur portion and wherein said second portion of said knee joint is a tibia portion.

14. A method according to claim 13 wherein said artificial ligament is a solid core filament.

15. A method according to claim 14, wherein said ligament housing is also an adjustable first housing according to claim 1.

16. A first housing to be implanted into a bone bore, said first housing containing a step shoulder which connects a first bore and a second bore (wherein said first bore and said second bore are both located substantially longitudinally within but both are not located coaxially within said first housing), and said first housing comprising also a third bore having a centerline which intersects said step shoulder at an angle of about 90°, said third bore being adapted to house a set screw.

* * * * *